(12) United States Patent
Reinmann

(10) Patent No.: US 7,766,881 B2
(45) Date of Patent: Aug. 3, 2010

(54) IMPLANT WITH SURFACE STRUCTURE

(75) Inventor: Andreas Reinmann, Bern (CH)

(73) Assignee: Roche Diagnostics International AG, Steinhausen (CH)

( * ) Notice: Subject to any disclaimer, the term of this patent is extended or adjusted under 35 U.S.C. 154(b) by 654 days.

(21) Appl. No.: 10/788,886

(22) Filed: Feb. 27, 2004

(65) Prior Publication Data

US 2005/0004526 A1   Jan. 6, 2005

Related U.S. Application Data

(63) Continuation of application No. PCT/CH02/00461, filed on Aug. 23, 2002.

(30) Foreign Application Priority Data

Aug. 31, 2001   (DE) .............................. 101 42 637

(51) Int. Cl.
*A61M 5/32* (2006.01)
(52) U.S. Cl. ..................................... 604/175
(58) Field of Classification Search ................ 604/175, 604/502, 288.01–288.04, 174, 285; 128/899; 427/2.14
See application file for complete search history.

(56) References Cited

U.S. PATENT DOCUMENTS

| | | | | |
|---|---|---|---|---|
| 3,638,649 A | | 2/1972 | Ersek | |
| 3,783,868 A | * | 1/1974 | Bokros | 604/891.1 |
| 4,025,964 A | * | 5/1977 | Owens | 623/11.11 |
| 4,183,357 A | * | 1/1980 | Bentley et al. | 604/175 |
| 5,098,397 A | * | 3/1992 | Svensson et al. | 604/175 |
| 5,098,398 A | | 3/1992 | Lundgren | |
| 5,219,361 A | * | 6/1993 | von Recum et al. | 623/23.74 |
| 5,370,698 A | | 12/1994 | Heimke et al. | |
| 5,507,815 A | | 4/1996 | Wagner et al. | |
| 5,662,616 A | * | 9/1997 | Bousquet | 604/175 |
| 5,830,191 A | * | 11/1998 | Hildwein et al. | 604/175 |
| 5,833,641 A | | 11/1998 | Curtis | |
| 6,096,070 A | * | 8/2000 | Ragheb et al. | 623/1.39 |
| 6,099,508 A | * | 8/2000 | Bousquet | 604/175 |
| 6,270,475 B1 | * | 8/2001 | Bestetti et al. | 604/93.01 |
| 6,459,917 B1 | * | 10/2002 | Gowda et al. | 600/345 |

OTHER PUBLICATIONS

Sbarbati, R, et al. Pyrolytic Carbon coating enhances Teflon and Dacron fabric compatibility with endothelial cell growth. 1991. Int J Artificial Organs. as read online at: http://www.ncbi.nlm.nih.gov/entrez/query.fcgi?cmd=Retrieve&db=PubMed&list_uids=1834590&dopt=Abstract.*

* cited by examiner

*Primary Examiner*—Nicholas D Lucchesi
*Assistant Examiner*—Christopher D Koharski
(74) *Attorney, Agent, or Firm*—Dorsey & Whitney LLP

(57) ABSTRACT

An implant with a surface structure on at least a portion of a surface of the implant, wherein the surface structure is selected to facilitate, improve and enhance ingrowth characteristics of the implant. A method of providing an implant with a selected surface structure is encompassed.

20 Claims, 2 Drawing Sheets

IMPLANT WITH SURFACE STRUCTURE

CROSS-REFERENCE TO RELATED APPLICATION(S)

This application is a continuation of International Application No. PCT/CH02/00461, filed on Aug. 23, 2002, which claims priority to German Application N. 101 42 637.2, filed on Aug. 31, 2001, the contents of which is incorporated herein in its entirety by reference.

BACKGROUND

The present invention relates to medical technology, including implantable devices. More particularly, it relates to an implant with a surface structure, in particular to a transcutaneous implant with an orientated structure on a surface thereof, which improves the ingrowth characteristics of the implant, and to a method for producing such an implant.

Implants are known which are inserted completely or partially into a body, wherein—for example in the case of an inserted port body—a region or portion of the port body protrudes out from the surface of the skin. This often results in problems with the surrounding skin growing onto the port body. Inflammations often form in the border region between the surrounding skin and the port body, which spread along the inserted port body into a patient's body. This is at least unpleasant for a patient, and leads to the port body being badly fitted and to a high risk of infection for the patient.

A device for promoting wound healing is known from U.S. Pat. No. 5,833,641, which consists of a biologically tolerable material and is bio-degradable. This device is used on a wound for wound healing and comprises a surface structure which serves to orientate a desired cellular growth and can be bio-degraded during or after the application, i.e. absorbed by the patient.

BRIEF SUMMARY

It is an object of the present invention to provide an implant which, once inserted, is more tolerable for a patient. Furthermore, it is an object of the present invention to provide a method for producing said implant.

In one embodiment, the present invention comprises an implant with a surface structure on at least a portion of a surface of the implant, wherein the surface structure is selected to facilitate, improve and enhance ingrowth characteristics of the implant. A method of providing an implant with a selected surface structure is encompassed.

One embodiment of an implant in accordance with the present invention is a transcutaneous implant, i.e., an implant which is not completely inserted into a body, such that after the implant has been inserted or implanted, at least a part of it protrudes out from the surface of the skin. An example of such an implant involves a port body which serves to introduce a substance into a subcutaneous tissue.

In accordance with one embodiment of the present invention, a surface structure is provided on at least one surface region of an implant, said surface structure improving the ingrowth characteristics of the implant. The surface structure is orientated such that the growth of cellular tissue around the implant is promoted and/or is assisted in one or more directions, including a preferred direction or preferred directions. The surrounding tissue can, for example, be skin cells, muscle cells or blood vessels. If skin cells are orientated in a uniform direction by such a surface structure of a transcutaneous implant, then the cellular arrangement arising—thus promoted by the surface structure—leads to an accelerated healing of the wound and an improved connection between the surrounding tissue cells and the implant wall, in particular in the structured region of the surface of the implant. Such an improved connection between the surrounding tissue cells and the implant also leads to improved protection from bacteria and undesirable matter, such that the risk of infection and inflammation when and after the implant is inserted is reduced. Using a suitable surface structure, the surface of the implant can be more densely populated by the surrounding tissue, thus improving cell adhesion to the implant wall.

In some embodiments, an implant in accordance with the present invention is preferably produced at least partially from a suitable durable, non-absorbable material such as metal, plastic or a combination thereof, such that the implant is not degraded after it has been inserted.

Advantageously, one embodiment of an implant in accordance with the present invention exhibits a suitable surface structure in the region where it penetrates the skin, wherein the surface structure particularly preferably runs roughly parallel to the surface of the skin when and after the implant is inserted.

Providing a surface structure which promotes the growth of cellular structures, in particular blood vessels, parallel to the available tissue, i.e., for example, parallel to the surface of the skin, leads to the blood vessels accumulating mainly parallel to the surface of the skin around the implant and away from the implant, and substantially not reaching deep along the implant wall. Such an arrangement of the blood vessels around the implant leads to better blood circulation in the surrounding tissue and is furthermore advantageous since infections which may occur on the surface of the skin cannot easily spread along the implant wall to deeper regions. Infections can therefore be more effectively controlled by the body's own defences and may be recognized earlier by the patient.

In some embodiments, including preferred embodiments, the structure on the surface of the implant is advantageously 1 to 10 mm wide, particularly preferably 4 to 5 mm wide, such that when the implant is inserted, surrounding tissue along this width of the surface structure can be orientated to a depth of 1 to 10 mm, preferably 4 to 5 mm, and can grow orientated onto the implant.

In some embodiments, the surface structure is advantageously arranged encircling at least a partial region of the implant, embodied for example—if the implant has a circular or oval cross-section—in the region where it passes through the surface of the skin, as a groove structure encircling the implant. In some embodiments, said groove structure preferably exhibits a uniform orientation, i.e., the individual grooves are generally parallel to each other.

In some preferred embodiments, the surface structure is particularly preferably embodied as a groove structure, for example as an encircling, spiral or helical groove or plurality of grooves. However, in some embodiments, the surface structure can be provided only on particular regions of the implant, other surface regions of the implant not comprising a surface structure, such that, for example, only individual grooves or groove structure sections are provided on the surface of the implant and are interrupted by a smooth surface of the implant. These embodiments are particularly useful if, for example, a desired orientation of cellular growth is only desired in or adjacent to a selected region of the surface of the implant.

In some embodiments, the depth of the grooves is preferably in the range of 0.1 to 10 times—particularly preferably, in the range of 0.3 to 5 times—the average width of the type of cell which is to grow onto or into the groove, wherein the average width of the type of cell is understood as the width when the cell is placed onto a flat surface.

In some embodiments, the depth of one or all of the grooves is advantageously in the range of 1 to 10 μm, preferably in the range of 3 to 4 μm, and the width of a groove is advantageously in the range of 1 to 10 μm, particularly preferably in the range of 4 to 5 μm.

In some embodiments, the groove distance, i.e., the distance from the centre of a groove to the centre of another groove, is advantageously in the range of 2 to 20 μm and is preferably 10 μm.

In some embodiments, the ratio of the width of the groove to the depth of the groove is advantageously in the range of 0.5 to 2, preferably substantially 1:1.

In some embodiments of the present invention, preferably at least two, more preferably three to ten or more, regions or areas on the surface of the implant are provided with a different surface structure, such that, for example, a first surface structure is provided in the region near the surface of the skin after the implant is inserted, in order to enable skin cells to grow, and one or more other surface structures are provided beneath this first surface structure, to promote the growth of subcutaneous cellular structures such as, for example, blood vessels or the like.

Advantageously, in some embodiments, a lower holding structure is provided on the implant and is inserted into the tissue. In one embodiment, this lower holding structure is a ring encircling the underside of the implant and protruding from the implant, in order to help hold the inserted implant. Advantageously, in some embodiments, passages or holes can be provided at one or more points on the encircling ring, through which tissue can grow in order to help better fit the implant. A recess, for example a groove, can advantageously be provided in the attachment region of the encircling ring, and surrounding tissue can grow into said recess, such that the fit of the implant is further improved.

In some embodiments, the implant is preferably a transcutaneous implant, such as a port body, and comprises a suitable connecting structure, such as a thread or other suitable holding elements such as recesses with protrusions, in the upper region, the region which protrudes out of the tissue when the implant is inserted. In some embodiments a connecting element can be attached to said connecting structure in order to be able to introduce a substance from an external source into the tissue through the port body, wherein the port body can for example have an opening on its underside through which a substance introduced from the upper side enters the tissue.

In accordance with another aspect of the present invention, a method for producing an implant as described above is provided, wherein a surface structure which improves the ingrowth characteristics of the implant is produced on at least a partial region or area of the surface of the implant.

In one embodiment, the selected surface structure can, for example, be achieved by mechanically producing a groove structure on the surface, wherein for example a spiral groove is produced directly on the surface of the implant, such that the groove leads spirally around, for example, a cylindrical implant wall. The spiral groove can be produced in a turning method process using a specially ground steel shape. It is advantageous, once the groove has been produced, to polish the implant along the groove or grooves produced, such that the surface is substantially smooth. This rounds but nonetheless maintains the grooves. The implant can then advantageously be anodised or eloxed, wherein an oxide layer is formed which also extends over the structured region of the implant.

It is equally possible to use an etching method to produce a desired surface structure, for example by means of an applied etching template. In this way, surface regions which are not to be etched are protected by an acid-resistant layer. Using an etching method, a multitude of different surface structures can be produced in one process.

DETAILED DESCRIPTION

Figure 1:
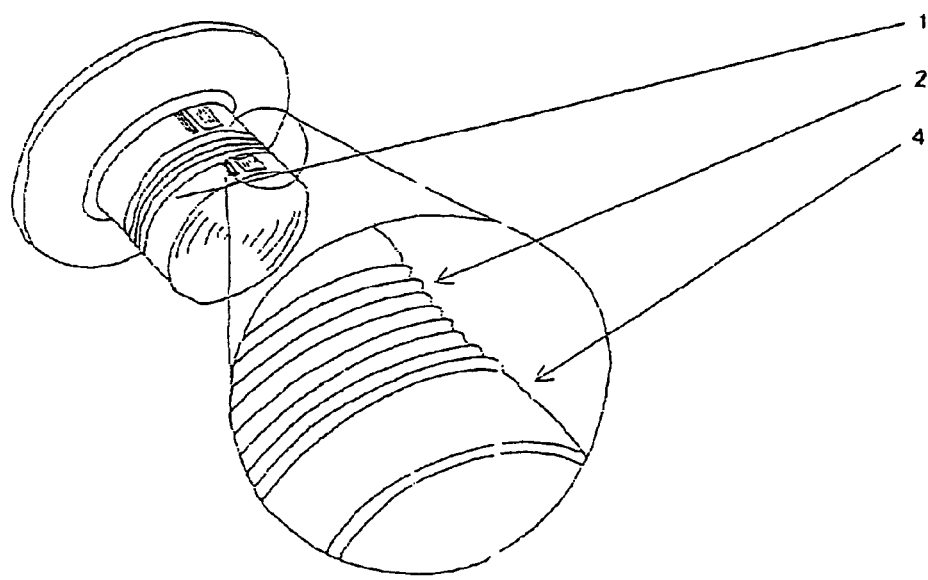
FIG. 1 depicts one embodiment of an implant in accordance with the present invention, with an enlarged partial region of the surface.

FIG. 1 shows an implant 1 which on a region of the implant wall 4 comprises a structured surface region 2 in the form of encircling grooves. If the implant 1 is inserted in the tissue such that the grooves 2 are in the region of the surface of the skin and are substantially parallel to the surface of the skin, then the encircling grooves promote the growth of skin cells in a direction along the grooves and thus help the tissue to grow in better and the implant to be held more securely.

Figure 2:
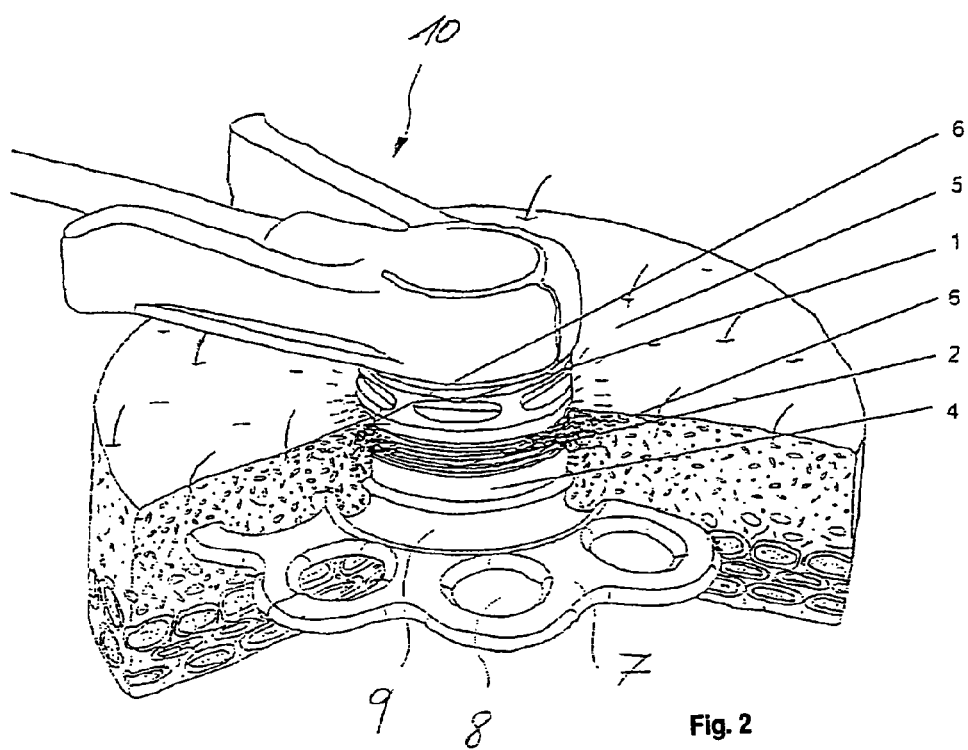
FIG. 2 depicts one embodiment a port body inserted in a tissue, the port body having a surface structure in accordance with the present invention.
Figure 3:
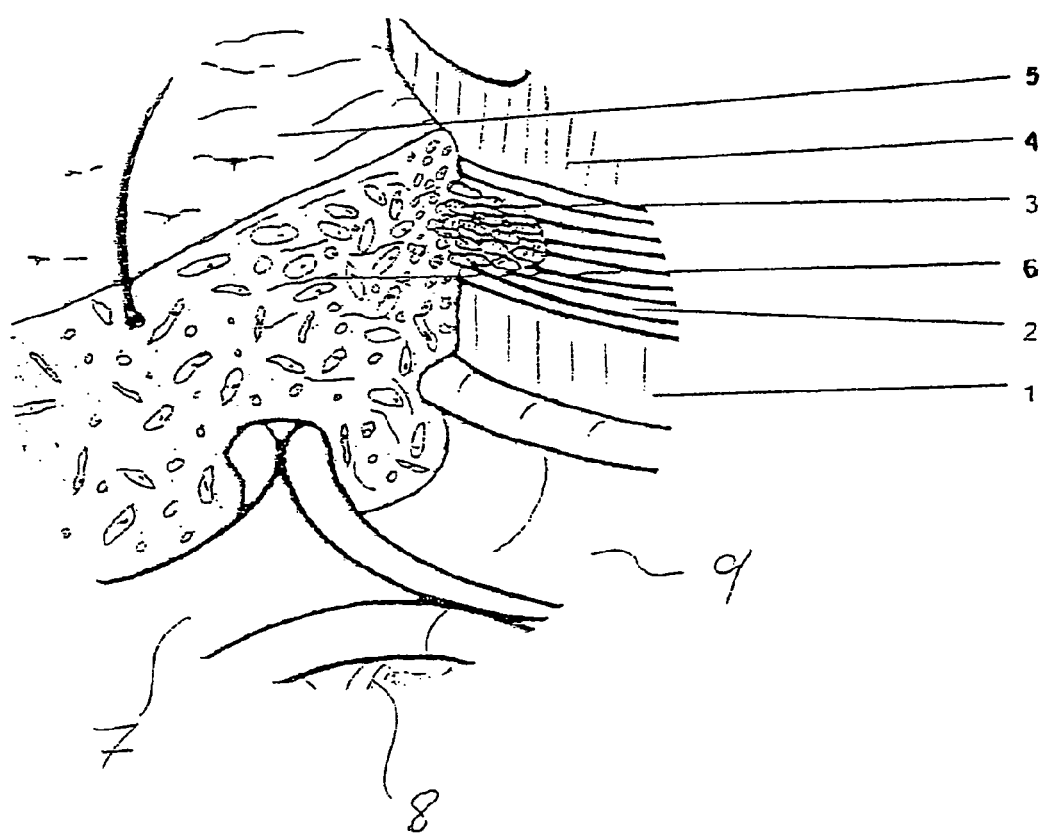
FIG. 3 is an enlargement of a partial region of the port body shown in FIG. 2.

FIG. 2 shows a port body 1 inserted into a tissue, with an encircling surface structure 2 in the form of an encircling spiral groove. As can be seen in particular from FIG. 3, tissue cells 3—such as for example skin and muscle cells and also blood vessels 6—accumulate along the orientated groove structure 2, which enables the tissue 3 to densely populate the surface 4 of the port body, parallel to the surface of the skin. Such a dense tissue cell population leads to an improved connection, i.e., to the tissue 3 growing into the port body 1 better, which enables the port body 1 to be more securely and firmly held. The cellular structure, thus orientated by the encircling groove structure 2, also stimulates the blood vessels 6 to orientate themselves parallel to the available tissue 3, such that the blood vessels 6 predominantly run mainly parallel to the surface 5 of the skin, around the port body 1. This promotes the blood circulation in the tissue region surrounding the port body 1, and largely prevents infection from spreading deep into the tissue.

Beneath the structured surface 2 of the port body 1, an implant wall 4 is formed which is substantially smooth on the surface, wherein surrounding tissue simply grows onto or lies on said implant wall 4, as in implants known from the prior art. A protruding ring 7 which encircles the underside of the port body 1 ensures that the inserted implant 1 is held better in the tissue 3. The ring 7 is interrupted by a number of holes 8 through which tissue can grow in order to further improve how the port body 1 is held or anchored in the tissue 3. On the attachment region of the ring 7 on the port body 1, a groove 9 is provided which the tissue 3 can grow into.

The portion or region of the port body 1 protruding out from the tissue on the surface 5 of the skin comprises a connecting structure (not shown), to which a connecting element 10 can be attached, in order to introduce a substance from an external storage container through the implant body 1 into the tissue 3. The port body can comprise an opening (not shown) on its underside through which the substance is dispensed from the port body 1 into the surrounding tissue.

As used herein, the phrase "surface structure" is intended to encompass, without limitation, suitable surface characteristics, textures, constructions, patterns, knurling, degree of roughness or smoothness, and the like. Suitable surface structure or structures in desired areas or regions of the surface of an implant or implantable device may be provided or produced by using any suitable method, for example, by casting, molding, cutting, abrading, laminating, coating, etching and the like. Suitable surface structure or structures may be formed integrally with an implant, eroded into the implant, and/or added, attached or connected thereto.

In the foregoing description, embodiments of the present invention, including preferred embodiments, have been presented for the purpose of illustration and description. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

I claim:

1. A method for inserting an implant into tissue, the method comprising the steps of:
   providing an implant, the implant comprising:
      a port structure comprising an outer wall having a substantially uniform outer circumference interrupted by a plurality of regions having areas of a smaller outer circumference, wherein a first region of the plurality of regions comprises one or more discrete tactile surface structures, and a second region of the plurality of regions comprises a plurality of discrete tactile surface structures, wherein each of said discrete tactile surface structures encircles the port structure and are arranged along a length of the port body that comprises at least a portion of an implant area;
      a holding structure coupled to a first end of the port structure, the holding structure comprising an encircling ring protruding from the first end of the port structure, the encircling ring comprising a plurality of openings spaced around said encircling ring; and
      a connecting structure coupled to a second end of the port structure and configured for conditional attachment to a connecting element; and
   inserting the implant into the tissue such that at least a portion of each of said discrete tactile surface structures is beneath an outer surface of the tissue and improves ingrowth characteristics associated with the implant by promoting growth of cellular tissue in at least one direction relative to the surface of the implant, and at least a portion of the connecting structure is provided above the outer surface of the tissue.

2. The method as set forth in claim 1, wherein the implant comprises a non-biosorbable material.

3. The method as set forth in claim 2, wherein one of the plurality of regions of tactile surface structure is provided in a region of the implant, wherein, after the implant has been implanted in a body, the surface structure is generally adjacent to the skin.

4. The method as set forth in claim 1, wherein the each of the tactile surface structures exhibits a width of approximately 1 to 10 mm.

5. The method as set forth in claim 1, wherein each of the tactile surface structures exhibits a width of approximately 4 to 5 mm.

6. The method as set forth in claim 1, wherein one or more of the tactile surface structures comprises a groove.

7. The method as set forth in claim 6, wherein the depth of said at least one or more grooves is approximately 0.1 to 10 times the average width of a type of cell adjacent to the groove after the implant is implanted.

8. The method as set forth in claim 6, wherein the depth of said at least one or more grooves is approximately 0.3 to 5 times the average width of a type of cell adjacent to the groove after the implant is implanted.

9. The method as set forth in claim 6, wherein the depth of the at least one groove is approximately 1 to 10 µm.

10. The method as set forth in claim 6, wherein the depth of the at least one groove is approximately 3 to 4 µm.

11. The method as set forth in claim 6, wherein the width of the at least one groove is in the range of approximately 1 to 10 µm.

12. The method as set forth in claim 6, wherein the width of the at least one groove is in the range of approximately 4 to 5 µm.

13. The method as set forth claim 6, wherein, if more than one groove is provided, the distance of the grooves from each other is approximately 2 to 20 µm.

14. The method as set forth claim 6, wherein, if more than one groove is provided, the distance of the grooves from each other is approximately 10 µm.

15. The method as set forth in 6, wherein the ratio of the width of the groove to the depth of the groove is approximately 0.5 to 2.

16. The method as set forth in claim 1, wherein the plurality of tactile surface structures promote growth of cellular tissue in a direction parallel to a skin surface into which the implant is inserted.

17. The method as set forth in claim 1, wherein the plurality of tactile surface structures promote growth of cellular tissue by orienting cell growth in a uniform direction relative to the surface structure of the implant.

18. A method for inserting an implant into tissue, the method comprising the steps of:
   providing an implant, the implant comprising:
      a port structure comprising an outer wall having a substantially uniform outer circumference having regions of interruptions, the regions comprising areas of a smaller outer circumference, wherein a first region interrupting the substantially uniform outer circumference comprises one or more discrete tactile surface structures, and wherein a second region interrupting the substantially uniform outer circumference comprises a plurality of discrete tactile surface structures, wherein the first and second region are separated by a portion of the outer wall having the substantially uniform outer circumference, and wherein each of said discrete tactile surface structures encircles the port structure and are arranged along a length of the port body that comprises at least a portion of the implant area;
      a holding structure coupled to a first end of the port structure, the holding structure comprising an encircling ring protruding from the first end of the port structure, the encircling ring comprising a plurality of openings spaced around said encircling ring; and
      a connecting structure coupled to a second end of the port structure and configured for conditional attachment to a connecting element; and
   inserting the implant into the tissue such that at least a portion of each of said discrete tactile surface structures is beneath an outer surface of the tissue and improves ingrowth characteristics associated with the implant by promoting growth of cellular tissue in at least one direction relative to the surface of the implant.

19. A method for inserting an implant into tissue, the method comprising the steps of:
   providing an implant, the implant comprising:
      a port structure comprising an outer wall having a first region and a second region, each of the first and second regions having a substantially smooth surface, and a surface structure region disposed between the first and second regions, wherein the surface structure region comprises a plurality of discrete surface structures encircling the port structure;
      a holding structure coupled to a first end of the port structure, the holding structure comprising an encircling ring protruding from the first end of the port structure, the encircling ring comprising a plurality of openings spaced around said encircling ring; and
      a connecting structure coupled to a second end of the port structure and configured for conditional attachment to a connecting element; and
   inserting the implant into the tissue such that at least a portion of each of said first, second, and surface structure regions is beneath an outer surface of the tissue, and at least a portion of the connecting structure is provided above the outer surface of the tissue.

20. The method as set forth in claim 19, wherein the holding structure further comprises an attachment region configured for coupling the holding structure to the first end of the port structure, and wherein the attachment region includes a circumferential recess in an outer surface thereof.

* * * * *